United States Patent [19]
LeBoulch et al.

[11] Patent Number: 5,631,162
[45] Date of Patent: May 20, 1997

[54] RETROVIRAL VECTORS FOR TRANSDUCING β-GLOBIN GENE AND β-LOCUS CONTROL REGION DERIVATIVES

[75] Inventors: Philippe LeBoulch; Irving M. London, both of Cambridge; Dorothy Tuan, Newton, all of Mass.

[73] Assignee: Massachusetts Institute of Technology, Cambridge, Mass.

[21] Appl. No.: 76,090

[22] Filed: Jun. 11, 1993

[51] Int. Cl.$^6$ .......................... C12N 15/64; C12N 15/68; C12N 15/85; C12N 15/86
[52] U.S. Cl. .................. 435/320.1; 435/69.1; 435/172.3
[58] Field of Search .............................. 435/320.1, 69.1, 435/172.3

[56] References Cited

U.S. PATENT DOCUMENTS 5,126,260  6/1992  Tuan et al. .......................... 435/240.2

OTHER PUBLICATIONS

McIvor (1990), Virol. 176: 652–655.
Yu et al. (1986) PNAS vol. 83: 3194–3198.
Miller et al. (1989) BioTechniques vol. 7(9): 980–988.
Collis et al. (1990) EMBO J vol. 9(1): 233–240.
Miller et al. (1988) J. Virol. vol. 62(11): 4337–4343.
Bender, M.A., et al., "A majority of mice show long–term expression of a human β–globin gene after retrovirus transfer into hematopoietic stem cells", *Mol. Cell. Biol.*, 9:1426–1434 (1989).
Chang, J.C., et al., "A 36–base–pair core sequence of locus control region enhances retrovirally transferred human β–globin gene expression", *Proc. Natl. Acad. Sci. USA*, 89:3107–3110 (1992).
Cone, R.D., et al., "Regulated expression of a complete human β–globin gene encoded by a transmissible retrovirus vector", *Mol. Cell Biol.*, 7:887–897 (1987).
Curtin, P.T., et al., "Human β–globin gene expression in transgenic mice is enhanced by a distant DNase I hypersensitive site", *Proc. Natl. Acad. Sci. USA*, 86:7082–7086 (1989).
Danos, O. and R.C. Mulligan, "Safe and efficient generation of recombinant retroviruses with amphotropic and ecotropic host ranges", *Proc. Natl. Acad. Sci. USA*, 85:6460–6464 (1988).
Dzierzak, E.A., et al., "Lineage–specific expression of a human β–globin gene in murine bone marrow transplant recipients reconstituted with retrovirus–transduced stem cells", *Nature*, 331:35–41 (1988).
Forrester, W.C., et al., "Molecular analysis of the human β–globin locus activation region", *Proc. natl. Acad. Sci. USA*, 86:5439–5443 (1989).
Fraser, C.C., et al., "Expansion in vitro of retrovirally marked totipotent hematopoietic stem cells", *Blood*, 76:1071–1076 (1990).
Fraser, C.C., et al., "Proliferation of totipotent hematopoietic stem cells in vitro with retention of long–term competitive in vivo reconstituting ability", *Proc. Natl. Acad. Sci. USA*, 89:1968–1972 (1992).

(List continued on next page.)

*Primary Examiner*—Mindy Fleisher
*Assistant Examiner*—Nancy J. Degen
*Attorney, Agent, or Firm*—Arnall Golden & Gregory

[57] ABSTRACT

A process and means for the design and the optimization of retroviral vectors transducing human β–globin gene and β–Locus Control Region (β–LCR) derivatives, hereafter referred to as [β–globin/LCR] retroviruses, which successfully meet the following criteria required for gene therapy applications: (1) stability of proviral transmission (low frequency of rearrangements similar to retroviral vectors considered stable in the art) upon infection of cell–lines and murine bone marrow cells, (2) improved viral titer, thereby allowing successful infection of bone marrow cells, and (3) high erythroid expression of the transduced human β–globin gene, are described, along with specific constructs.

38 Claims, 9 Drawing Sheets

OTHER PUBLICATIONS

Gallie, D.R., et al., "The 5'-leader sequence of tobacco mosaic virus RNA enhances the expression of foreign gene transcripts in vitro and in vivo", *Nucleic Acids Res.*, 15:3257–3273 (1987).

Grosveld, F., et al., "Position–independent, high–level expression of the human β–globin gene in transgenic mice", *Cell*, 51:975–985 (1987).

Hawley, T.S., et al., "Comparative analysis of retroviral vector expression in mouse embryonla carcinoma cells", *Plasmid*, 22:120–131 (1989).

Humphries, R.K., et al., "Self–renewal of hemopoietic stem cells during mixed colony formation in vitro", *Proc. Natl. Acad. Sci. USA*, 78:3629–3633 (1981).

Karlsson, S., et al., "Expression of the human β–globin gene following retroviral–mediated transfer into multipotential hematopoietic progenitors of mice", *Proc. Natl. Acad. Sci. USA* 85:6062–6066 (1988).

Krainer, A.D. and T. Maniatis, (1988) In Hames, B., D., and Glover, D., M. (ed.), "RNA splicing", *Transcription and Splicing* (IRL Press, Oxford), pp. 131–206.

Lemischka, I.R., et al., "Developmental potential and dynamic behavior of hematopoietic stem cells", *Cell*, 45:917–927 91986).

Nev, P.A., et al., "Tandem AP–1–binding sites within the human β–globin dominant control region function as an inducible enhancer in erythroid cells", *Genes Dev.*, 4:993–1006 (1990).

Novak, U., et al., "High–level β–globin expression after retroviral transfer of locus activation region–containing human β–globin gene derivatives into murine erythroleukemia cells", *Proc. Natl. Acad. Sci. USA*, 87:3386–3390 (1990).

Parkman, B., "The application of bone marrow transplantation to the treatment of genetic diseases", *Science*, 232:1373–1378 (1986).

Philipsen, S., et al., "The β–globin dominant control region: hypersensitive site 2", *EMBO J.*, 9:2159–2167 (1990).

Pruzina, S., et al., "Hypersensitive site 4 of the human β–globin locus control region", *Nucleic Acids Res.*, 19:1413–1419 (1991).

Ryan, T.M., et al., "A single erythroid–specific DNase I super–hypersensitive site activates high levels of human β–globin gene expression in transgenic mice", *Genes Dev.*, 3:314–323 (1989).

Talbot, D., et al., "Detailed analysis of the site 3 region of the human β–globin dominant control region", *EMBO J.*, 9:2169–2178 (1990).

Tuan, D., et al., "The β–like–globin gene domain in human erythroid cells", *Proc. Natl. Acad. Sci. USA*, 82:6384–6388 (1985).

Tuan, D.Y.H., et al., "An erythroid–specific, developmental–stage–independent enhancer far upstream of the human β–like globin genes", *Proc. Natl. Acad. Sci. USA*, 86:2554–2558 (1989).

Tuan, D. and I.M. London, "Mapping of DNase I–hypersensitive sites in the upstream DNA of human embryonic ε–globin gene in K562 leukemia cells", *Proc. Natl. Acad. Sci. USA*, 81:2718–2722 (1984).

Verma, I.M., "Retroviral vectors for gene transfer", In *Microbiology*–1985, American Society for Microbiology, pp. 229–232, Washington, 1985.

Walters, M., et al., "Characterization of a DNA binding activity in DNAse I hypersensitive site 4 of the human globin locus control region", *Nucleic Acids Res.*, 19:5385–5393 (1991).

FIG. 2a

Extended Ψ+

3' flanking region

β-globin gene

| | 5' SS | BPS + 3'SS | | Poly A |
|---|---|---|---|---|
| 1 | AGGTGAGc (III) | | | |
| 325 | | TTgGAa | TCTTgTCTgCTGCAG | |
| 406 | AGGTcAcT | gCCaGAC | TaCCaCTCCCTTaAG | |
| 430 | | | | |
| 501 | | TGTcAAg | CCTTCTgCTCTGCAG | |
| 774 | | CCTcGAT | CCTCCTTTaTCCAG | |
| 792 | | CCTcGAT | TCaCTCCTTCTCTAG | |
| * 847 | AGGTGgtT | TACaAAa | TCaaaTTCTTCTCAG | |
| * 1048 | | TACTAAg | CCagTCCTTCCAaAG | |
| * 1084 | ctGTGAGT | | | |
| * 1153 | | gTCaAAC | TTTTCCTTCTTTCaAG | |
| * 1212 | | gTCaAAC | TCCTTCTTCaagTAG | |
| * 1215 | | TTTgCAg | CCTTCTTTCaTGgAG | |
| * 1558 | | CACTGAC | aCaTTCCCTTTTTAG | |
| 1648 | | | | |
| * 1704 | | aATaAAAT | TTTTTTaTTaggCAG | |
| * 1712 | | TCCaGAa | TaTCCCCaGTTTAG | |
| * 1754 | | TTCatAa | CCCCaGTTTaGTAG | |
| 1756 | | gCCacAC | aCCaCTTTCTgATAG | |
| 1868 | | | | |
| 1899 | gGGTGAaT | | | |
| 1975 | AGGTAtGa (I) | | | AATAAA+[T]n |
| 2044 | | | | |
| 2173 | | CCTTAAC | aCTgTTaTTCTTTAG | |
| * 2409 | AGGTGAGc (III) | | | |
| * 2419 | | | | AATAAA |
| * 2647 | | | | |
| 2886 | | CACTAAa | CTTTCTTgCCaTgAAG | |
| 2920 | | aAcCCAa | TCTCCaCaTgCCCAG | |
| 3100 | | CACCAAC | CaCCTTgCCCCACAG | AATAAA |
| 3195 | | gCCCCAC | CagaCTTTCCTCCAG | AATAAA |
| * 3221 | | gCCCCAC | aCTTCTCCTCagGGAG | AATAAA |
| * 3224 | AtGTAAGc | | | |
| * 3298 | | | | |

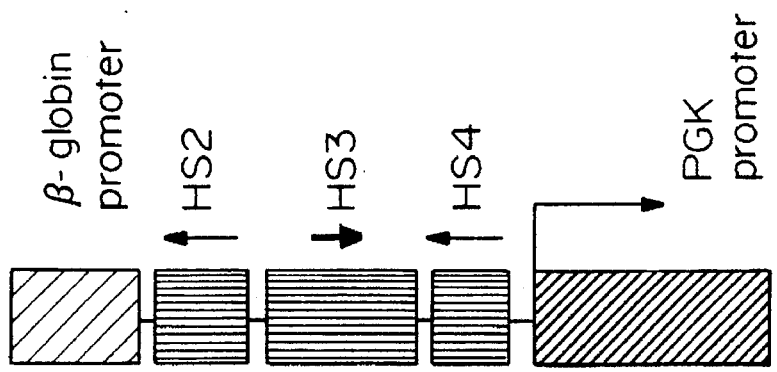

FIG. 2b

| | 5'SS | BPS + 3'SS | Poly A |
|---|---|---|---|
| 3355 | gGGTGAGg (III) | TGCccAg  CCCTgCTCCTgGgAG | |
| 3402 | | | |
| 3481 | | TTCaAAAC  agCCCCTCCCTCTaAAG | |
| 3543 | | TACaAAT  aTCCCTTTTgCaAAG | |
| 3578 | AGGTcAcT | TATTtAC  CaCaTTCTgTCTCAG | |
| 3889 | | | |
| 3956 | cGGTGActT | | |
| 4079 | AGGTGgtT | | |
| 4087 | AGGTcAGg (IV) | | |
| 4092 | AGGTtgGT | | |
| 4171 | AGGTGgGg | | |
| 4286 | gaGTGAGT | TCTgGAg  gCCCTggCTCTGCAG | |
| 4349 | | | |
| 4529 | AGGTcAaT | TCTaGAT  TCCCCCgggCTGCAG | |
| 4554 | | aTTctAC  CTTTTCCCaagGCAG | |
| 4582 | | no BPS  CTaCTCCTCCCTAG | |
| 4728 | | no BPS  TCCTCCCCTagTCAG | |
| 4732 | | CCCCtAg  CCCCCGgCCCCGCAG | |
| 4754 | | | |
| 4924 | | TCCTcAT  gCCTTTCggCTGCAG | |
| 5065 | gGGTGgGT | | |

FIG. 3e
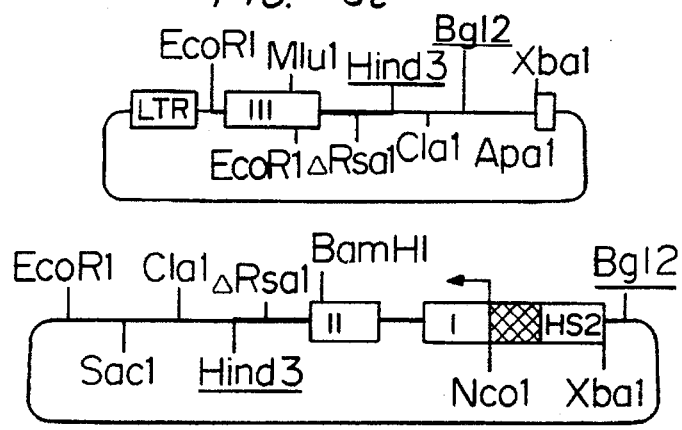
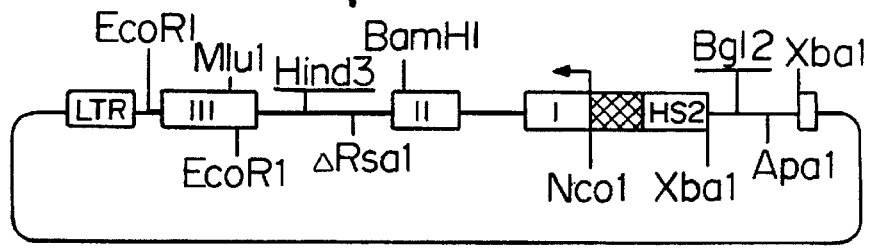
FIG. 3f
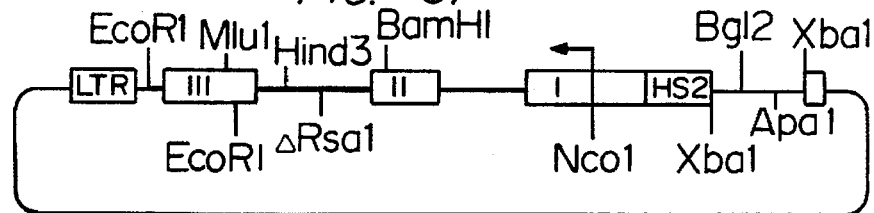
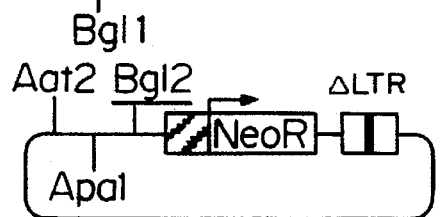
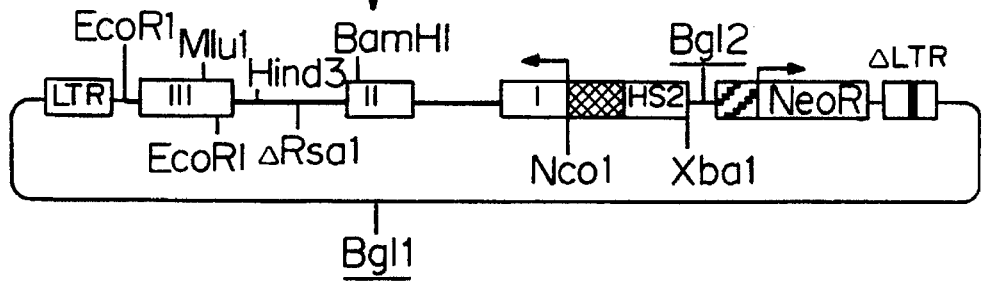

FIG. 4a

```
                    (1665)                                    ↓ Exon III
--GAATTC--  aaatattcag  aaataattta  aatacatcat  tGCAATGAAA  ATAAATGTTT
                                                                A
                                                              PolyA
EcoR1
◄─────────────────────────────────────────────────────────────────
                                                             (1770)
TTTATTAGGC  AGAATCCAGA  TGCTCAAGGC  CCTTCATAAT  ATCCCCCAGT  TT AGTAG TTG
         G                                               T     CGC
     3'SS                                            3'SS      3'SS
─────────────────────────────────────────────────────────────────► Mlu 1

GACTTAGGGA  ACAAAGGAAC  CTTTAATAGA  AATTGGACAG  CAAGAAAGCG  AGCTTAGTGA
         C
────────────────────►

TACTTGTGGG  CCAGGGCATT  AGCCACACCA  GCCACCACTT  TCTGATAGGC  AGCCTGCACT (1908)        δ-[Asn.Arg]                           Exon III
GGTGGGGT GA ATTG TTGCC  AAAGTGATGG  GCCAGCACAC  AGACCAGCAC  GTTGCCCAGG
                          T  C
         EcoR1
      ──────────────────────────────►
   ↓ Intron 2
AGCTGTGGGA  GGAAGATAAG  AGGTATGAAC  ATGATTAGCA  AAAGGGCCTA  GCTTGGACTC

AGAATAATCC  AGCCTTATCC  CAACCATAAA  ATAAAAGCAG  AATGGTAGCT  GGATTGTAGC

TGCTATTAGC  AATATGAAAC  CTCTTACATC  AGTTACAATT  TATATGCAGA  AATATTTATA (2185)
TGCAGAAATA  TTGCTATTGC  CTTAACCCAG  AAATTATCAC  TGTTATTCTT  TAGAATGGTG
                                                            AAG CTT
                                                              3'SS
                                              ◄───────────────  Hind3

CAAAGAGGCA  TGATACATTG  TATCATTATT  GCCCTGAAAG  AAAGAGATTA  GGGAAAGTAT
────────────────────►
```

FIG. 4b

TAGAAATAAG ATAAACAAAA AAGTATATTA AAAGAAGAAA GCATTTTTTA AAATTACAAA

TGCAAAATTA CCCTGATTTG GTCAATATGT GTAC(2345)ACATAT TAAAACATTA CACTTTAACC
←————— Rsal —————→

CATAAATATG TATAATGATT ATGTATCAAT TGAAAATAAA AGAAAATAAA GTAGGGAGAT
             PolyA   PolyA TATGAATATG CAAATAAGCA CACATATATT CCAAATAGTA ATGTACTAGG CAGACTGTGT
                         Rsal

AAAGTTTTTT TTTAAGTTAC TTAATGTATC TCAGAGATAT TTCCTTTTGT TATACACAAT

GTTAAGGCAT TAAGTATAAT AGTAAAAATT GCGGAGAAGA AAAAAAAGA AAGCAAGAAT

TAAACAAAAG AAAACAATTG TTATGAACAG CAAATAAAAG AAACTAAAAC GATCCTGAGA
          PolyA (2717)
CTTCCACACT GATGCAATCA TTCGTCTGTT TCCCATTCTA AACTGTACCC TGTTACTTCT
                        Rsal →

FIG. 4c

CCCCTTCCTA TGACATGAAC TTAACCATAG AAAAGAAGGG GAAAGAAAAC ATCAAGGGTC

Intron 2 ↓ Exon II       (2820)
CCATAGACTC ACCCTGAAGT TCTCA`GGATC C`ACGTGCAGC TTGTCACAGT GCAGCTCACT ← BamH1

CAGTGTGGCA AAGGTGCCCT TGAGGTTGTC CAGGTGAGCC AGGCCATCAC TAAAGGCACC

GAGCACTTTC TTGCCATGAG CCTTCACCTT AGGGTTGCCC ATAACAGCAT CAGGAGTGGA

Exon II ↓
CAGATCCCCA AAGGACTCAA AGAACCTCTG GGTCCAAGGG TAGACCACCA GCAGCCTAAG

Intron 1

GGTGGGAAAA TAGACCAATA GGCAGAGAGA GTCAGTGCCT ATCAGAAACC CAAGAGTCTT

Intron 1
CTCTGTCTCC ACATGCCCAG TTTCTATTGG TCTCCTTAAA CCTGTCTTGT AACCTTGATA

↓ Exon I                                                    LeuAla
CCAACCTGCC CAGGGCCTCA CCACCAACTT CATCCACGTT CACCTTGCCC CACAGGGCAG
                                                              AA
                                                            ← 3'SS Ser        Pro        His     (3250)
TAACGGCAGA CTTCTCCTCA GGAGTCAGGT GCA`CCATGG`T GTCTGTTTGA GGTTGCTAGT
    G          G          A
            3'SS 3'SS
                                         NcoI
Exon I ←⁺¹ Promoter          (3325)
GAACACAGTT GTGTCAGAAG CAAATGTaag caatagatgg ctctgccctg

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 1666 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens
    ( G ) CELL TYPE: Beta-globin gene ( i x ) FEATURE:
    ( A ) NAME/KEY: misc_signal
    ( B ) LOCATION: 37..298
    ( D ) OTHER INFORMATION: /note= "Exon III"

( i x ) FEATURE:
    ( A ) NAME/KEY: misc_signal
    ( B ) LOCATION: 299..1148
    ( D ) OTHER INFORMATION: /note= "Intron 2"

( i x ) FEATURE:
    ( A ) NAME/KEY: misc_signal
    ( B ) LOCATION: 1149..1370
    ( D ) OTHER INFORMATION: /note= "Exon II"

( i x ) FEATURE:
    ( A ) NAME/KEY: misc_signal
    ( B ) LOCATION: 1371..1501
    ( D ) OTHER INFORMATION: /note= "Intron 1"

( i x ) FEATURE:
    ( A ) NAME/KEY: misc_signal
    ( B ) LOCATION: 1502..1643
    ( D ) OTHER INFORMATION: /note= "Exon I"

( x i ) SEQUENCE DESCRIPTION: SEQ ID NO:1:

```
GAATTCAAAT ATTCAGAAAT AATTTAAATA CATCATTGCA ATGAAAATAA ATGTTTTTA      60
TTAGGCAGAA TCCAGATGCT CAAGGCCCTT CATAATATCC CCCAGTTTAG TAGTTGGACT    120
TAGGGAACAA AGGAACCTTT AATAGAAATT GGACAGCAAG AAAGCGAGCT TAGTGATACT    180
TGTGGGCCAG GGCATTAGCC ACACCAGCCA CCACTTTCTG ATAGGCAGCC TGCACTGGTG    240
GGGTGAATTC TTTGCCAAAG TGATGGGCCA GCACACAGAC CAGCACGTTG CCCAGGAGCT    300
GTGGGAGGAA GATAAGAGGT ATGAACATGA TTAGCAAAAG GGCCTAGCTT GGACTCAGAA    360
TAATCCAGCC TTATCCCAAC CATAAAATAA AAGCAGAATG GTAGCTGGAT TGTAGCTGCT    420
ATTAGCAATA TGAAACCTCT TACATCAGTT ACAATTTATA TGCAGAAATA TTTATATGCA    480
GAAATATTGC TATTGCCTTA ACCCAGAAAT TATCACTGTT ATTCTTTAGA ATGGTGCAAA    540
GAGGCATGAT ACATTGTATC ATTATTGCCC TGAAAGAAAG AGATTAGGGA AAGTATTAGA    600
AATAAGATAA ACAAAAAAGT ATATTAAAAG AAGAAAGCAT TTTTTAAAAT TACAAATGCA    660
AAATTACCCT GATTTGGTCA ATATGTGTAC ACATATTAAA ACATTACACT TTAACCCATA    720
AATATGTATA ATGATTATGT ATCAATTGAA AATAAAGAA ATAAAGTAG GGAGATTATG      780
AATATGCAAA TAAGCACACA TATATTCCAA ATAGTAATGT ACTAGGCAGA CTGTGTAAAG    840
TTTTTTTTTA AGTTACTTAA TGTATCTCAG AGATATTTCC TTTTGTTATA CACAATGTTA    900
AGGCATTAAG TATAATAGTA AAAATTGCGG AGAAGAAAAA AAAAGAAAGC AAGAATTAAA    960
CAAAAGAAAA CAATTGTTAT GAACAGCAAA TAAAAGAAAC TAAAACGATC CTGAGACTTC   1020
CACACTGATG CAATCATTCG TCTGTTTCCC ATTCTAAACT GTACCCTGTT ACTTCTCCCC   1080
TTCCTATGAC ATGAACTTAA CCATAGAAAA GAAGGGGAAA GAAAACATCA AGGGTCCCAT   1140
AGACTCACCC TGAAGTTCTC AGGATCCACG TGCAGCTTGT CACAGTGCAG CTCACTCAGT   1200
GTGGCAAAGG TGCCCTTGAG GTTGTCCAGG TGAGCCAGGC CATCACTAAA GGCACCGAGC   1260
ACTTTCTTGC CATGAGCCTT CACCTTAGGG TTGCCCATAA CAGCATCAGG AGTGGACAGA   1320
TCCCCAAAGG ACTCAAAGAA CCTCTGGGTC CAAGGGTAGA CCACCAGCAG CCTAAGGGTG   1380
```

| | | | | | |
|---|---|---|---|---|---|
| GGAAAATAGA | CCAATAGGCA | GAGAGAGTCA | GTGCCTATCA | GAAACCCAAG | AGTCTTCTCT | 1440 |
| GTCTCCACAT | GCCCAGTTTC | TATTGGTCTC | CTTAAACCTG | TCTTGTAACC | TTGATACCAA | 1500 |
| CCTGCCCAGG | GCCTCACCAC | CAACTTCATC | CACGTTCACC | TTGCCCCACA | GGGCAGTAAC | 1560 |
| GGCAGACTTC | TCCTCAGGAG | TCAGGTGCAC | CATGGTGTCT | GTTTGAGGTT | GCTAGTGAAC | 1620 |
| ACAGTTGTGT | CAGAAGCAAA | TGTAAGCAAT | AGATGGCTCT | GCCCTG | | 1666 |

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (G) CELL TYPE: Beta-globin gene (xi) SEQUENCE DESCRIPTION: SEQ ID NO:2:

ATTTATATGC AGAAATATT        19

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (G) CELL TYPE: Beta-globin gene (xi) SEQUENCE DESCRIPTION: SEQ ID NO:3:

GGAGAAGAAA AAAAAAGAAA G        21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens
        (G) CELL TYPE: Beta-globin gene (xi) SEQUENCE DESCRIPTION: SEQ ID NO:4:

AGAAAAGAAG GGGAAAGAAA A        21

( 2 ) INFORMATION FOR SEQ ID NO:5:

( i ) SEQUENCE CHARACTERISTICS:
    ( A ) LENGTH: 83 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens
    ( G ) CELL TYPE: Beta-globin gene ( i x ) FEATURE:
    ( A ) NAME/KEY: misc_feature
    ( B ) LOCATION: 22..23
    ( D ) OTHER INFORMATION: /note= "Substituted base or
          introduced base"

( i x ) FEATURE:
    ( A ) NAME/KEY: misc_feature
    ( B ) LOCATION: 56..60
    ( D ) OTHER INFORMATION: /note= "Substituted bases or
          introduced bases"

( x i ) SEQUENCE DESCRIPTION: SEQ ID NO:5:

```
CTGTGGGAGG AAGATAAGAG GGATGAACAT GATTAGCAAA AGGGCCTAGC TTGGACGCGT    60
CATCAAGGGT CCCATAGACT CAC                                            83
```

RETROVIRAL VECTORS FOR TRANSDUCING β-GLOBIN GENE AND β-LOCUS CONTROL REGION DERIVATIVES

This invention was made with government support under Grant Number NIH-HL48374 awarded by the National Institutes of Health. The government has certain rights in this invention.

The present invention is in the field of molecular genetics and, in particular, relates to the field of retroviral vectors and methods for making these vectors for transducing β-globin gene and β-locus control region derivatives.

BACKGROUND OF THE INVENTION

β-thalassemias and sickle-cell anemia are human genetic disorders of the β-globin gene, with severe clinical manifestations in homozygotes. At the present time, allogeneic bone marrow transplantation represents the best available possibility of cure for these patients. Unfortunately, few of them are able to locate a normal HLA-matched donor and even if a matched HLA donor were available, many would face severe complications of the bone marrow transplantation procedure such as graft versus host disease (Parkman, R., Science 232:1373–1378 (1986)). For these reasons, gene therapy using genetically modified autologous totipotent hematopoietic stem cells (THSC) is an attractive alternative to allogeneic bone marrow transplantation. Because gene targeting by homologous recombination is not yet technically possible in THSC, the most realistic strategy is to obtain stable integration of a normal human β-globin gene and its cis-acting regulatory elements into the THSC genome. This can be achieved by retrovirus-mediated gene transfer, an efficient gene transfer technique applicable to these cells (Fraser et al., Blood, 76:1071–1076 (1991)).

Gene transfer experiments have previously shown that the proximal cis-acting elements of the human β-globin gene are insufficient for gene therapy applications because they provide a very low, integration site-dependent expression of the human β-globin transgene (less than 1 to 5% of human β-globin/murineβ$_{maj}$-globin mRNA ratio) (Cone et al., Mol. Cell Biol. 7:887–897 (1987); Dzierzak et al., Nature 331:35–41 (1988); Karlsson et al., Proc. Natl. Acad. Sci. USA 78:3629–3633 (1988); Miller et al., J. Virol., 62:4337–4345 (1988); Bender et al., Mol. Cell. Biol., 9:1426–1434 (1989)). The discovery of major hypersensitive sites (HS) far upstream of the human β-globin gene locus, constituting the β-Locus Control region (β-LCR), has given new hope for successful gene therapy of human β-globin gene disorders. (Tuan and London, Proc. Natl. Acad. Sci. USA 81:2718–2722 (1984); Tuan et al., Proc. Natl. Acad. Sci. USA 82:6384–6388 (1985); Forrester et al., Proc. Natl. Acad. Sci. USA 89:1968–1972 (1986); Grosveld et al., Cell 51:975–985 (1987)). LCR derivatives are able to confer erythroid-specific, high, integration site-independent expression of a linked β-globin gene in transgenic mice and murine erythroleukemia (MEL) cells, which mimic adult erythroid differentiation (Grosveld et al., Cell 51:975–985 (1987)). Because the activity of each HS site has now been localized to small DNA fragments (U.S. Pat. No. 5,126,260; Curtin et al., Proc. Natl. Acad. Sci. USA 86:7082–7086 (1989); Forrester et al., Proc. Natl. Acad. Sci. USA 86:5439–5443 (1989); Ryan et al., Genes Dev. 3:314–323 (1989); Tuan et al., Proc. Natl. Acad. Sci. USA, 86:2554–2558 (1989); Collis et al., EMBO J., 9:233–240 (1990); Ney et al., Genes Dev. 4:993–1006 (1990); Philipsen et al., EMBO J., 9:2159–2167 (1990); Talbot et al., EMBO J., 9:2169–2178 (1990); Pruzina et al., Nucleic Acids Res., 19:1413–1419 (1991); Walters et al., Nucleic Acids Res., 19:5285–5393 (1991)), it has become possible to construct retroviral vectors transducing β-LCR derivatives linked to the human β-globin gene and its proximal cis-acting elements (Novak et al., Proc. Natl. Acad. Sci., USA, 87:3386–3390 (1990); Chang et al., Proc. Natl. Acad. Sci. USA, 89:3107–3110 (1992)). However, these [β-globin/LCR] retroviruses have low titer, are very unstable with multiple rearrangements upon transmission of the proviral structure, and provide a relatively modest and highly variable enhancement of β-globin gene expression in infected murine erythroleukemia (MEL) cells (Novak et al., Proc. Natl. Acad. Sci. USA 87:3386–3390 (1990); Chang et al., Proc. Natl. Acad. Sci. USA 89:3107–3110 (1992)).

U.S. Pat. No. 5,126,260 describes DNAaseI hypersensitive sites that constitute the β-LCR and, in particular, identifies the HS2 enhancer within the β-LCR structure. U.S. Pat. No. 5,126,260 also claims the use of β-LCR and HS2 derivatives in gene transfer protocols, including retrovirus-mediated gene transfer, to obtain high expression level of the human β-globin gene. However, U.S. Pat. No. 5,126,260 does not identify specific means by which stable proviral transmission of [β-globin/LCR] retroviruses can be achieved.

It is therefore an object of the present invention to provide retroviral vectors for stable transduction of the β-globin gene and β-locus control region derivatives and other erythroid specific genes.

SUMMARY OF THE INVENTION

Retroviral vectors capable of transducing the human β-globin gene and β-Locus Control Region (β-LCR) derivatives, hereafter referred to as the [β-globin/LCR] retroviral vectors, are provided. The [β-globin/LCR] retroviral vectors successfully meet the following criteria required for successful gene therapy: (1) stability of proviral transmission, or low frequency of rearrangements similar to retroviral vectors considered stable in the art, upon infection of cell-lines and murine bone marrow cells; (2) improved viral titer, thereby allowing successful infection of bone marrow cells; and (3) high erythroid expression of the transduced human β-globin gene, defined herein as greater than 50% of human β-globin to murine β$_{maj}$-globin mRNA ratio on a per gene basis in pools of infected and dimethylsulfoxide-induced (DMSO-induced) murine erythroleukemia (MEL) cells.

Specific constructs that meet the criteria presented above are described in detail below.

Specific means to design additional [β-globin/LCR] retroviral vectors meeting these criteria are also described.

The improved vectors are useful in the treatment of a variety of disorders including β-thalassemia and sickle-cell anemia.

BRIEF DESCRIPTION OF THE DRAWINGS

FIGS. 2A–2B is a DNA sequence analysis of [β-globin/LCR] constructs, screening for the presence of potential deleterious sequences such as 5' splice-sites (5'SS), 3' splice-sites (3'SS) and branchpoint sites (BPS), and polyadenylation signals (polyA). Matches or mismatches with consensus sequences are indicated by capital letters or lowercases, respectively. Regions mutated by site-directed mutagenesis or related procedures are indicated by an asterisk.

FIGS. 3A–F are schematic representations of the steps involved in the mutagenesis procedure used to produce the retroviral constructs of the present invention. The numbering system corresponds to that of FIGS. 2 and FIGS. 4A–4C. FIG. 3A shows PCR mediated deletion of the 372 bp [Rsa1-Rsa1] fragment in Intron 2. Two independent PCR reactions were performed using two pairs of primers overlapping the intragenic EcoR1 (1908), Rsa1 (2345), Rsa1 (2717) and BamH1 (2820) sites, respectively. In order to tag the coding region of the gene for further studies, mutations substituting two amino acids of β- with δ-globin amino acids were introduced in the EcoR1 primer. PCR products were digested with EcoR1, BamH1, and Rsa1. A triple ligation was subsequently performed with the parental [β-globin] vector opened at EcoR1 and BamH1 sites. FIG. 3B shows that region [1665 to 1770] was reconstituted and mutated by ligation of four complementary and overlapping oligonucleotides with the LXSN vector opened at EcoR1 and Xba1 sites. A polylinker was included in the oligonucleotide sequence, to prepare for subsequent steps of the construction. Only two of the four oligonucleotides were phosphorylated to prevent concatemerization upon ligation. The ligation product was digested with Xho1 prior to transformation to eliminate parental plasmid. FIG. 3C shows that region [1770 to 2185] was reconstituted and mutated by PCR mediated construction. Point mutations and additional restriction sites (Mlu1 and Hind3) were introduced in PCR primers. These new sites allowed ligation with the vector obtained in the step shown in FIG. 3B opened at Mlu1 and Hind3 sites. The ligation product was digested with BamH1 prior to transformation to eliminate parental plasmid. FIG. 3D shows that region [2185 to 3250] was reconstituted and mutated by PCR mediated construction, with an approach similar to the step shown in FIG. 3C. The template used contained the 372 bp intronic deletion obtained in the step shown in FIG. 3A. After cutting the vector and PCR fragment with Sac1 and Nco1, ligation was performed with a vector containing HS2, the β-globin promoter and the first part of the gene. The ligation product was digested with Sma1 prior to transformation to eliminate parental plasmid. FIG. 3E shows that the [Hind3-Bgl2] insert from the construct shown in FIG. 3D was ligated with the backbone of the construct shown in FIG. 3C opened with Hind3 and Bgl2. The ligation product was digested with Cla1 prior to transformation to eliminate parental plasmids and unwanted forms. FIG. 3F shows that the final [β-globin/HS2]$^{mut}$ retroviral construct was obtained by ligating a [Bgl1-Bgl2] fragment from the construct shown in FIG. 3E with a [Bgl2-Bgl1] fragment containing an enhancer/promoter/ NeoR cassette and a [Pvu2-Xba1] deleted MoMLV LTR. The ligation product was digested with Apa1 prior to transformation to eliminate parental plasmids and unwanted forms. Accuracy of the construct was verified by DNA sequencing.

FIG. 4 is the DNA sequence (Sequence Listing ID No. 1) of the retrovirally transduced human β-globin gene in C/R orientation, from base 1665 to 3325 according to the numbering system set forth in FIG. 2. The three exons, two introns, and promoter are indicated. The 372 bp [Rsa1-Rsa1] deletion in Intron 2 is underlined. Mutated PolyA and 3'SS are indicated. Point mutations introduced by mutagenesis are shown below the wild-type sequence. Codons maintained or substituted by corresponding codons from human δ-globin gene are indicated. Restrictions sites relevant to the mutagenesis are boxed and numbered. Oligonucleotides used for the mutagenesis are represented by arrows.

DETAILED DESCRIPTION OF THE INVENTION

Figure 1:
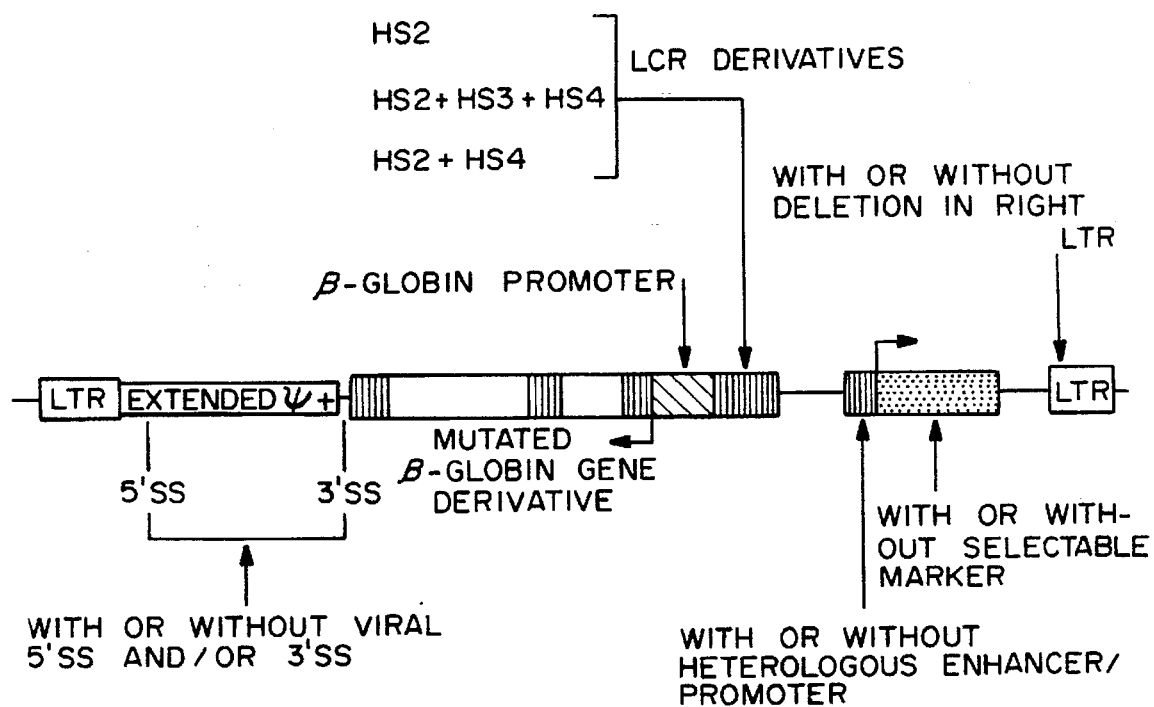
FIG. 1 is a schematic representation of the general design of the [β-globin/LCR] retroviral vectors of the present invention.

Retroviral vectors capable of transducing the human β-globin gene and β-Locus Control Region (β-LCR) derivatives (the [β-globin/LCR] retroviral vectors), for the treatment of disorders such as β-thalassemia and sickle-cell anemia by gene therapy, and methods for producing these vectors are provided. These [β-globin/LCR] retroviral vectors are superior to currently available retroviral vectors in that they (1) exhibit stable proviral transmission with a low frequency of rearrangements upon infection of cell-lines and murine bone marrow cells, (2) produce higher viral titers, thereby allowing successful infection of bone marrow cells, defined herein as greater than $10^5$ G418 resistant NIH 3T3 colonies per ml of viral supernatant under standard conditions, and (3) cause high erythroid expression of the transduced human β-globin gene, defined herein as greater than 50% of human β-globin to murine$_{maj}$-globin mRNA ratio on a per gene basis in pools of infected and dimethylsulfoxide-induced (DMSO-induced) murine erythroleukemia (MEL) cells.

Structures believed to be responsible for the proviral instability and low titer of [β-globin/LCR] retroviral vectors currently available have now been identified. These structures include an A/T rich segment in the second intron of the human β-globin gene, and several complementary/reverse (C/R) polyadenylation signals and splice-sites. Extensive mutagenesis of the transduced β-globin gene that results in elimination of these structures renders proviral transmission stable upon infection of cell-lines and murine bone marrow stem cells, increases viral titer ten-fold, and does not significantly perturb the expression of the transduced β-globin gene. The optimized retroviral vectors described herein have enabled study of the expression properties of various retrovirally-transduced β-LCR derivatives in DMSO-induced MEL cells and achievement of greater than 50% of human β-globin/murine$_{maj}$-globin mRNA ratios on a per gene basis. The question of position-independent expression following chromosomal integration has also been addressed. The influence of heterologous enhancers/promoters on the expression of the retrovirally transduced β-globin gene, when cis-linked to β-LCR derivatives, has also been analyzed.

As used herein, a retrovirus is an animal virus belonging to the virus family of Retroviridae, including any types, subfamilies, genus, or tropisms.

Retroviral vectors, in general, are described by Verma, I. M., Retroviral vectors for gene transfer. In MICROBIOLOGY-1985, American Society for Microbiology, pp. 229–232, Washington, 1985, which is incorporated by reference herein.

Identification of DNA Sequences Deleterious for Stability and Titer of [β-globin/LCR] Retroviruses The structures believed to be responsible for the proviral instability and low titer were identified by the following procedure. A computer search for DNA sequences within β-globin gene and β-LCR derivatives that could be potential causes of retroviral rearrangements was conducted. Two general mechanisms of retroviral instability have been previously described: (1) inappropriate splicing or polyadenylation creating deletions in the viral genomic RNA, and/or (2) rearrangements during the steps of reverse transcription often triggered by various types of repeated sequences. The computer search was therefore conducted for a virtual concatemer representing a 5 kb DNA segment composed, from 5' to 3', of the 814 bp hybrid extended packaging signal (Ψ+); the 2748 bp fragment containing the human β-globin gene and its promoter, in complementary/reverse (C/R) orientation; the 374 bp HS2 fragment, in C/R orientation; the 287 bp HS3 fragment, in direct orientation; the 243 bp HS4 fragment, in C/R orientation; the 583 bp murine phosphoglycerate kinase-1 (PGK) promoter, in direct orientation. Elements upstream or downstream of this 5 Kb segment were not included in this search, because rearrangements in LTRs or markers for antibiotic resistance (Neo$^R$) would most likely not be compatible with viral transmission of G418 resistance.

Five C/R [AATAAA] cleavage/polyadenylation (polyA) signals were identified, all located in the β-globin gene, as shown in FIGS. 2 and 4. No strong downstream polyA element such as [T]n, [GT]n, or [YGTGTTYY] was detected for most of them, except for polyA at position 1704 in FIG. 2, which is followed by nine [T] in an 11 bp segment immediately downstream. For splicing signals, the consensus described in vertebrate animals reported by Krainer and Maniatis, (1988) In Hames, B., D., and Glover, D., M. (ed.), TRANSCRIPTION AND SPLICING. (IRL Press, Oxford) pp. 131–206): $[G_{38}/A_{39}A_{62}G_{77}G_{100}T_{100}A_{60}A_{74}G_{84}T_{50}]$ for 5'SS, $[Y_{77}Y_{78}Y_{81}Y_{83}Y_{89}Y_{85}Y_{82}Y_{81}Y_{86}Y_{91}Y_{87}NY_{97}A_{100}G_{100}]$ for 3'SS, and $[Y_{13/16}NY_{16/16}T_{14/16}R_{13/16}A_{16/16}Y_{15/16}]$ for branchpoint sites (BPS), 2 to 21 bp upstream of a putative 3'SS. In addition, potential 5'SS were grouped according to the following five classes previously described by Krainer and Maniatis, supra (1988): class I=AGGTA; class II=GTAAG; class III=RGGTGAG; and class IV=AGGTNNGT.

Eighteen potential 5'SS with two mismatches or fewer, and thirty-two potential 3'SS with three mismatches or fewer were identified, as shown in FIGS. 2 and 4. With regard to direct repeats, a region very rich in A/T, including degenerated tandem direct repeats of motifs such as [AAAAT]n or the variant [AAAAN]n, was noted in Intron 2, as shown in FIG. 4. Three of the C/R polyA sites are present in this A/T rich area, which has also been reported by Miller et al., *J. Virol.* 62:4337–4345 (1988) to have a possible deleterious effect on the propagation of [β-globin] retroviral vectors. Another extended direct tandem repeat [ATTTATATGCAGAAATATT] (Sequence Listing ID No. 2) was found in Intron 2, as shown in FIG. 4. No homology was detected with constitutive retroviral elements such as Ψ+, tRNA primer binding site (PBS), or LTR including the integration (IN) motif. No strong homology with the polypurine track for RNAase H cleavage of viral genomic RNA and initiation of positive-strand strong-stop was detected, although two polypurine segments in Intron 2 were identified: [GGAGAAGAAAAAAAAAGAAAG] (Sequence Listing ID No. 3) and [AGAAAAGAAGGGGAAAGAAAA] (Sequence Listing ID No. 4), as shown in FIG. 4. No extended inverted repeats were detected.

Description of Specific [β-globin/LCR] Retroviral Constructs Useful for Gene Therapy The general design of the [β-globin/LCR] retroviral vectors of the present invention is described in FIG. 1. The β-globin gene is inserted in reverse orientation with respect to the direction of transcription of the provirus, to prevent splicing of the β-globin introns on the viral genomic RNA prior to reverse transcription. All the constructs in these examples are derived from the LXSN vector (Miller and Rosman, *BioTechniques*, 7:980–990 (1989), the teachings of which are incorporated by reference herein), however, any other retrovirus-based vector can be used.

The principal features of LXSN (Dusty Miller, The Fred Hutchinson Center, Seattle, Wash.) include from 5' to 3': the left LTR of Moloney murine sarcoma virus (MoMSV), the tRNA primer binding site (PBS) of MoMSV, a hybrid extended packaging signal (Ψ+) described below, a polylinker for DNA insertion, an internal SV40 enhancer/early promoter driving a NeoR gene, the polypurine track of Moloney murine leukemia virus (MoMLV), and the right LTR of MoMLV. Ψ+ extends into the gag region for production of high titer viruses. To prevent expression of MoMLV gp85 and p65 gag proteins, the p65 gag start codon of this vector is mutated into a stop codon and the upstream part of the vector (left LTR up to the 5' part of Ψ+) is substituted with homologous sequences from MoMSV which does not express gp85 gag. This region also contains a hybrid intron with 5'SS from MoMSV and cryptic 3'SS from MoMLV.

The 5' border of the human β-globin promoter is the SnaB1 site 266 bp upstream of the CAP site. The 3' border was optimized by removing most of the 3' flanking region of the human β-globin gene. Only 30 bp downstream of the gene were retained, to allow normal cleavage/polyadenylation of the human β-globin gene. The right LTR was kept intact, or a self-inactivating vector was designed, by creating in the 3' LTR of LXSN, a 176 bp [Pvu2-Xba1] deletion described previously in pZipNeoSV(X)1 by Cone et al., *Mol. Cell Biol.* 7:887–897 (1987) and Dzierzak et al., *Nature* 331:35–41 (1988), the teachings of which are incorporated by reference herein.

With respect to the LCR derivatives, all constructs contain a 374 bp [Hind3-Xba1] fragment containing the HS2 enhancer described in U.S. Pat. No. 5,126,260, the teachings of which are incorporated herein.

In addition to the HS2 enhancer, one construct contains a 287 bp HS3 fragment obtained by PCR starting 21 bp upstream [AGACCCT . . . ] and ending 41 bp downstream [ . . . CCTATAC] of the 225 bp [Hph1-Fnu4H1] HS3 core described by Philipsen et al., *EMBO J.* 9:2159–2167 (1990) and a 243 bp HS4 fragment obtained by PCR starting 27 bp downstream [GGGTATA . . . ] and ending at the Ava1 site of the 280 bp [Sst1-Ava1] HS4 core fragment described by Pruzina et al., *Nucleic Acid. Res.* 19:1413–1419 (1991). Another construct contains only the above described HS4 fragment next to the HS2 enhancer fragment, without HS3.

SV40 enhancer/early promoter driving NeoR of LXSN was substituted by the F441 Py enhancer/TK promoter/NeoR cassette of PMC1neo (Stratagene, San Diego, Calif.) or a murine phosphoglycerate kinase (PGK-1) promoter/NeoR cassette (obtained from Rudolf Jaenisch, The Whitehead Institute, Cambridge, Mass.). In some constructs, the heterologous enhancer/NeoR cassette was deleted, to increase viral titer, although no selection was now possible.

Selection markers that can be inserted into the retroviral vectors include in addition to the neomycin/G418 resistance gene, a hygromycin resistance gene, a puromycin resistance gene, a phleomycin resistance gene, a dihydrofolate reductase gene, and a multidrug-resistance gene. Other markers that can be used include any molecule, such as the gene encoding β-galactosidase, which interacts with a substrate to produce a colored cell, or a molecule expressed at the cell membrane and used in a cell sorting procedure, for example by interaction with a specific antibody.

Characteristics of the Modified Transduced β-globin Gene and β-LCR Derivatives The foregoing modifications of the transduced β-globin gene and β-LCR derivatives caused increased viral titer, restored stability of proviral transmission in cell-lines and bone marrow stem cells, and did not impair expression of the transduced β-globin gene.

Figure 3A:
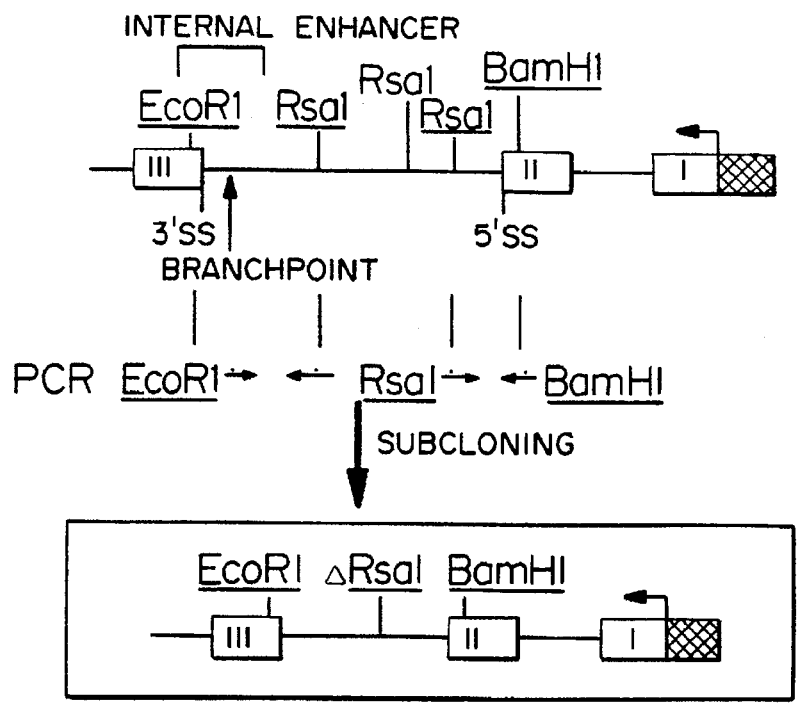
Figure 3B:
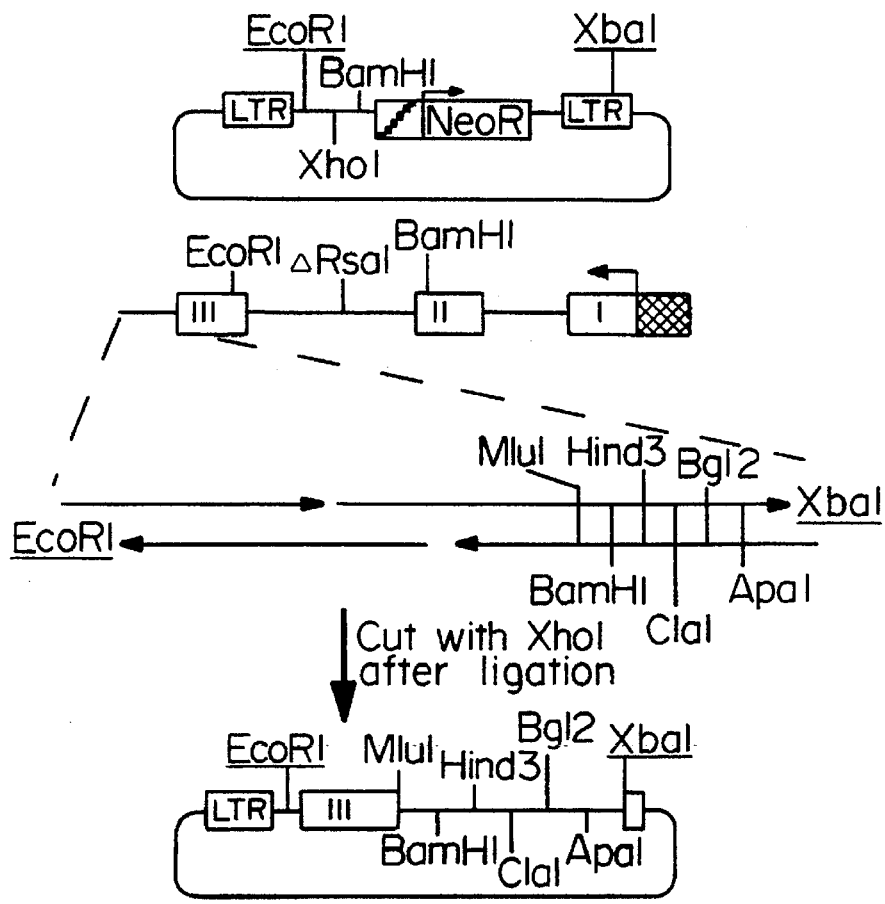
Figure 3C:
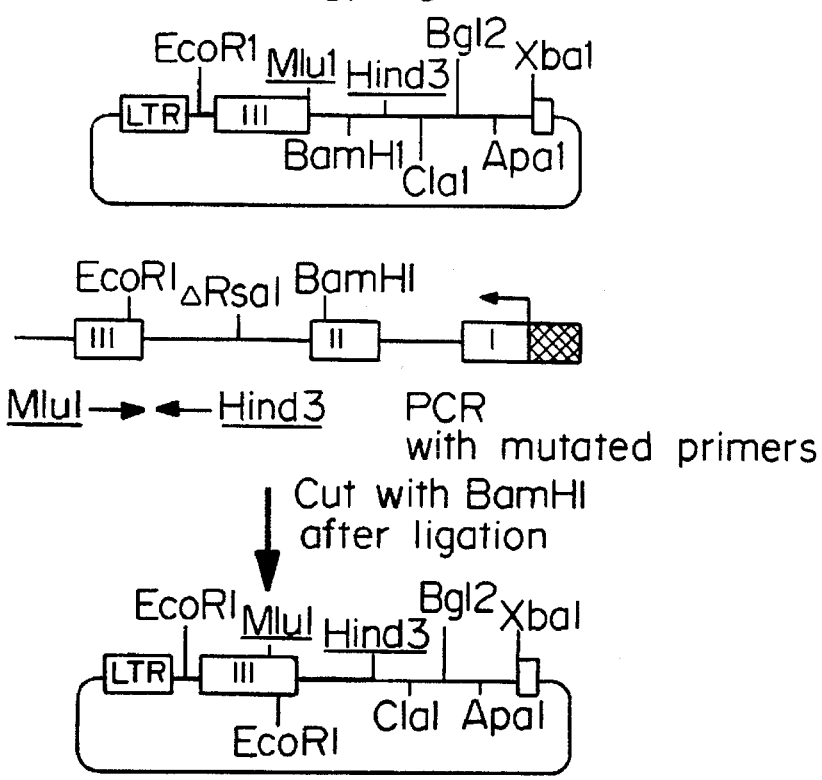
Figure 3D:
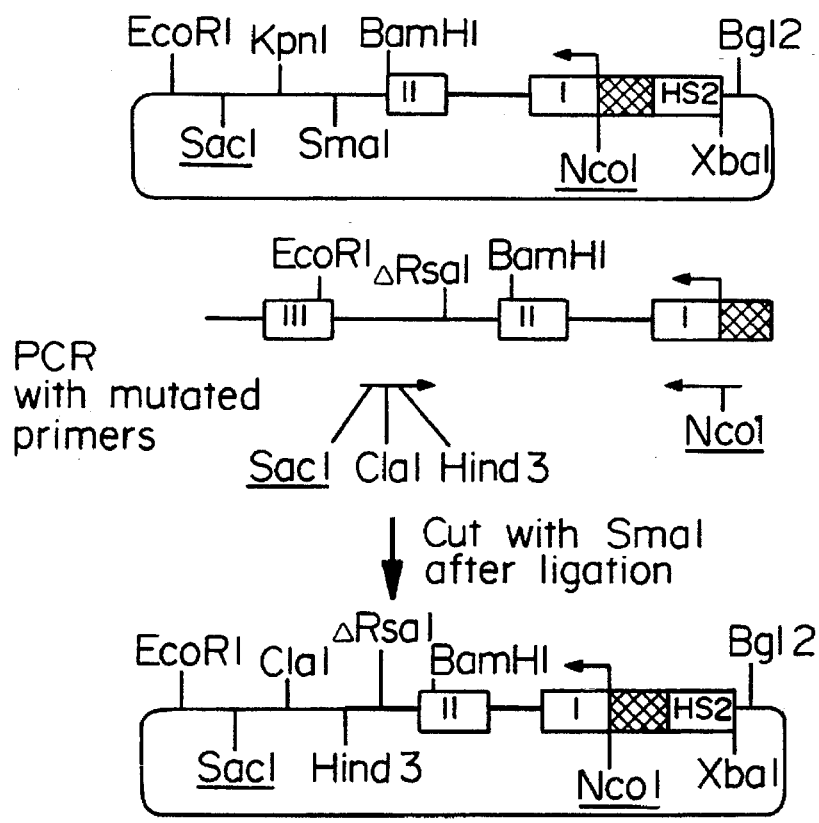

Initially, the removal of DNA segments potentially deleterious for titer and stability, which were likely to be neutral for β-globin gene expression, was attempted. A 372 bp fragment of Intron 2 between two Rsa1 sites respectively located at +580 and +952 from the human β-globin cap site was deleted. This deleted fragment contains most of the satellite DNA-like A/T rich segment, three of the five potential polyA sites, and one of the polypurine tracks. This deleted segment is clearly distant from essential intronic structures such as normal 5'SS, 3'SS, branchpoint, and intragenic enhancer. Since Rsa1 sites are frequent cutters, this deletion was performed by recombinant PCR, as shown in FIGS. 3A and 4.

The results indicate that the 372 bp deletion in Intron 2 and the shortening of the 3' flanking region increase viral titer of [β-globin/LCR] constructs by ten-fold (Table I), but is not capable in itself to prevent instability of proviral transmission in the presence of complex β-LCR derivatives such as [HS2+HS3+HS4].

two mismatches were mutated. In addition, one point mutation was created in the polyA at position 1704, as shown in FIG. 2, which is followed by a strong downstream [GT]/[T] region. A total of twenty point mutations were introduced in this first phase of the mutagenesis, by a complex multistep construction procedure described in FIG. 3.

These additional mutations restored stability of proviral transmission in cell-lines and bone marrow stem cells, and did not impair expression of the transduced β-globin gene. These optimized [β-globin/LCR] retroviruses are referred hereafter as to [β-globin/LCR]$^{mut}$.

In order to stabilize further proviral transmission in some constructs, the 340 bp [BamH1-Xho1] fragment of pZipNeoSV(X)1 containing the 3'SS of Moloney MLV used to generate the sub-genomic "ENV" transcript was inserted in some constructs. This fragment appeared either neutral, useful or deleterious depending on the construct used.

Stability of Proviral Transmission Upon Infection of Cell-lines and Murine Bone Marrow Stem Cells Proviral transmission of [β-globin/LCR]$^{mut}$ viruses was tested upon infection of NIH 3T3 and MEL cells with

TABLE I

Comparison of transmission and expression properties of [β-globin/LCR] retroviruses.

| Type | human β$^a$ Murine β$_{maj}$ + $_{min}$ | human β$^a$ Murine β$_{maj}$ | Viral Titer$^b$ |
|---|---|---|---|
| pZipneoSV(X)β-globin(RO) enh + c | 2% | 5% | 2 × 10$^4$ |
| [β-globin/HS2/SV40]$^d$ | 27% | 63% | 10$^4$ |
| [β-globin/SV40]$_{mut}$ | 11% | 27% | 2 × 10$^5$ |
| [β-globin/HS2/SV40]$_{mut}$ | 26% | 69% | 10$^5$ |
| [β-globin/HS2/F441 Py]$_{mut}$ | 32% | 73% | 10$^5$ |
| [β-globin/HS2/PGK]$_{mut}$ | 29% | 70% | 4 × 10$^5$ |
| [β-globin/(HS2 + [4 × 23 bp HS2])/PGK]$_{mut}$ | 18% | 46% | 2 × 10$^5$ |
| [β-globin/(HS2 + HS3 + [4 × CP2 HS4])/PGK]$_{mut}$ | 36% | 76% | 2 × 10$^4$ |
| [β-globin/(HS2 + HS3 + HS4)/PGK]$_{mut}$ | 38% | 82% | 10$^4$ |

$^a$Pool of greater than 100 G418 resistant MEL cell clones. Corrected values for specific activities of the probes and on a per gene basis (one proviral copy per cell in pseudo-diploid MEL cells)
$^b$Titers of best ψcre producers, measured by transmission of G418 resistance to NIH 3T3 cells (cfu/ml).
$^c$Construct provided by R. Mulligan, Whitehead Insitute and MIT, Cambridge, MA, and described by Cone, et al., Mol. Cell Biol. 7:887–897 (1987) and Dzierzak, et al., Nature 331:35–41 (1988)
$^d$Deletion of part of the 3' flanking region of transduced human β-globin gene was observed with this construct.

A more extended deletion of 774 bp in Intron 2 was also performed, with similar results. The sequence of this new intron, constructed by oligonucleotide-mediated construction, is CTGTGGGAGGAAGATAAGAGG GATGAACATGATTAGCAAAAGGGCCTAGCT TGGA CGCGTCATCA AGGGTCCCATAGACTCAC (represented in complementary/reverse orientation; bases substituted or introduced are underlined) (Sequence Listing ID No. 5).

In an additional effort to stabilize proviral transmission of [β-globin/LCR] retroviral vectors, extended site-directed mutagenesis was performed to eliminate other complementary/reverse potential SS and polyA signals. Because there were indications that most of the rearrangements occurred in the transduced β-globin gene, the focus was directed toward potential SS sites located in the β-globin gene itself, and the first phase of mutagenesis limited to 3'SS. In this process, care was taken not to alter known cis-acting features and coding regions. Accordingly, seven of the ten potential C/R 3'SS localized in the β-globin gene were destroyed by point mutation in [AG], as shown in FIG. 4. In particular, all the potential 3'SS presenting one or supernatant from producers generated with these constructs. Southern blot analysis of genomic DNA from infected and G418 selected cells demonstrated stable proviral transmission with all constructs, even in the presence of [HS2+HS3+ HS4] derivatives and when infection was performed with pool of producers. Only a minor rearranged component (less than 10%) was detected in a pool of infected cells generated from viruses containing (HS2+HS3+[4×CP2 of HS4]). When independent producer clones were analyzed, most expressed a non-rearranged form. To detect microrearrangements that could have escaped this analysis, genomic DNA from infected and G418 selected cells was digested with Sma1, which is located in both LTR's as well as between β-LCR derivatives and the internal PGK/NeoR cassette. The internal Sma1 site was always conserved, confirming the absence of microdeletion in this proviral region. Although Novak et al., Proc. Natl. Acad. Sci., USA 87:3386–3390 (1990) and Chang et al., Proc. Natl. Acad. Sci., USA 89:3107–3110 (1992) have reported that [β-globin/LCR] retroviral constructs have the propensity to undergo additional rearrangements after multiple passages of producers, no such rearrangements were observed, even after several weeks of continuous culture.

To further challenge the stability of mutated vectors, an intact right LTR was introduced in the [β-globin/HS2/PGK]$^{mut}$ construct, and a "ping-pong" infection was performed by co-cultivation of amphotropic Ψcrip and ecotropic Ψcre producers for two weeks. No rearrangement was observed following this challenge. Packaging cells Ψcre and Ψcrip (Danos and Mulligan, Proc. Natl. Acad. Sci. USA, 85:6460–6464 (1988)), provided by Richard Mulligan (Whitehead Institute and MIT, Cambridge, Mass.) were grown at 37° C. with 5% $CO_2$/95% air in Dulbecco's modified Eagle's medium (DMEM) supplemented with 10% calf serum, 100 IU/ml penicillin and 100 mg/ml streptomycin. Plasmid DNAs used for transfection were prepared by the Quiagen procedure, according to protocol provided by the manufacturer (Quiagen, Inc., Chatsworth, Calif.). Because self-inactivating vectors were used, plasmid DNAs were directly transfected in packaging cells using a calcium phosphate procedure (5prime:3prime, Inc), after linearization of the plasmids outside the proviral structure (Nde1 site). Following G418 selection (500 mg/ml of active fraction) (Gibco, BRL, Gaithersburg, Md.), pool of producers or independent producer clones were isolated and expanded. In the case of "ping-pong" experiments using non-self-inactivating vectors, Ψcre and Ψcrip producers were mixed and co-cultivated for 10 days. Producer cells were used directly for infection by co-cultivation, or viruses were prepared by filtration of supernatant through 0.45 mm Millipore filter, as described by Danos and Mulligan, Proc. Natl. Acad. Sci. USA 85:6460–6464 (1988).

Viral titers obtained with these vectors are presented in Table I above. To test whether [β-globin/LCR]$^{mut}$ vectors are able to transmit correct proviral structure to hematopoietic stem cells, murine bone marrow cells were infected with pool of producers from 5-fluorouracil (5-FU) treated donor mice. Two constructs were chosen: [β-globin/HS2/PGK]$^{mut}$ because of higher titer, and [β-globin/(HS2+HS3+[4×CP2 of HS4])/PGK]$^{mut}$ because the minor rearranged component observed with this construct could indicate a tendency for instability and would represent additional challenge. An "empty" Zen vector (titer greater than $10^6$/ml) (described by Fraser et al., Blood, 76:1071–1076 (1991)) was used as a control. Infected bone marrow was plated for in vitro clonogenic assays to estimate gene transfer efficiency, or was transplanted into lethally irradiated syngeneic mice. Gene transfer efficiency was estimated by comparing the number of macroscopic CFU-Mix-Erythroid colonies in the presence or in the absence of G418.

Bone marrow cells were isolated from adult male (C57BL/6J×C3H/HeJ)F1 mice injected intravenously four days previously with 5-FU (150 mg/Kg). For infection, $6×10^6$ bone marrow cells were added to 90% confluent irradiated (15 Gy x-ray) viral producer cells in 100 mm Petri dishes in α-medium containing 10% FCS, 5% CS (for Ψcre derived β-globin viral producers) or 5% newborn calf serum (for GP-E86-derived JZenNeo viral producers), 5% pokeweed mitogen-stimulated spleen cell conditioned medium, 100 ng/ml murine Steel factor (Immunex, Seattle, Wash.) and 4 μg/ml Polybrene™ (Sigma, St. Louis, Mo.). Co-cultivation were performed for two days, with or without selection (prior to assay) in G418 (500 (active) μg/ml) for one additional day. Non-adherent and adherent cells, recovered by trypsinization, were combined for clonogenic progenitor assays or transplantation into irradiated (9.5 Gy $^{137}$Cs) recipient mice. Transplant recipients received $2×10^6$ pre-infection cell equivalents intravenously and were sacrificed three weeks later for DNA isolation from the spleen. For clonogenic progenitor assays, cells were plated at 1.5× $10^4$ pre-infection cell equivalents in 35 mm Petri dishes in 1.1 ml of a culture medium containing 0.8% methylcellulose, 30% FCS, 1% bovine serum albumin, $10^{-4}$M β-mercaptoethanol, 3 units/ml human urinary erythropoietin, 2% Pokeweed mitogen-stimulated spleen cell conditioned medium and 10% agar stimulated human leukocyte conditioned medium (Media Preparation Service, Terry Fox Laboratory, Vancouver, Canada), with or without G418 (0.8 (active) μg/ml). After 18 days incubation, macroscopic-erythroid colonies were scored by standard criteria described by Humphries et al., Proc. Natl. Acad. Sci. USA 78:3629–3633 (1981). Dishes were then flooded with phosphate buffered saline (PBS) and cells recovered by centrifugation for subsequent RNA isolation and analysis.

Gene transfer efficiencies were estimated at about 60% for the Zen vector and approximately 40% for [β-globin/LCR]$^{mut}$ vectors. Genomic DNA from whole spleens of reconstituted animals was prepared at day 13 post-engraftment. Southern blot analysis performed subsequently showed that gene transfer into hematopoietic stem cells was obtained in all transplanted mice. Correct proviral transmission with no detectable rearrangement was observed in the three mice receiving the [HS2/β-globin/PGK]$^{mut}$ vector. The two mice receiving [β-globin/(HS2+HS3+[4×CP2 of HS4])/PGK]$^{mut}$ showed different ratios of the two forms observed upon infection of cell-lines with this virus. This difference in ratio is likely to be a consequence of the oligo-clonality of bone-marrow reconstitution following engraftment, based on results obtained by Lemischka et al., Cell 45:917–927 (1986) and Fraser et al., Proc. Natl. Acad. Sci. USA 89:1968–1972 (1991). No additional rearranged form was detected.

Mutations are Neutral for Expression of the Transduced β-globin Gene

It was next determined whether extended mutagenesis was deleterious for β-globin gene expression. RNA protection assays using appropriate probes demonstrated that mutated human β-globin mRNA was properly initiated and spliced in infected MEL cells. Mutated human β-globin mRNA also appeared correctly initiated and spliced in cells obtained from in vitro clonogenic assays following infection of murine bone marrow stem cells. Furthermore, the level of expression of the human β-globin transgene in DMSO-induced MEL cells infected with [β-globin/LCR]$^{mut}$ viruses was similar to the gene expression level obtained with non-mutated [β-globin/LCR] constructs electroporated into MEL cells.

High and Erythroid Expression of the Transduced Human β-globin Gene in Infected and DMSO-induced MEL Cells To obtain preliminary indications on gene expression, linearized plasmids containing various [β-globin/LCR] inserts in the context of a proviral structure were electroporated into MEL cells. Semi-adherent (APRT-) MEL cells, provided by Paul-Henri Romeo (INSERM U91, Paris, France), were grown at 37° C. with 5% $CO_2$/95% air in DMEM supplemented with 12% horse serum, 4.5 μg/ml glucose, 2 mM glutamine, 100 IU/ml penicillin and 100 μg/ml streptomycin. Electroporations were performed with approximately $10^7$ MEL cells/ml in DMEM and 20 μg of plasmid DNA linearized with Nde1, using the Cellporator (BRL) with the following set-up: low resistance, capacitance 1180 μF, and in the range of 250–350 V. Infections of MEL cells were performed with 3 ml of filtered supernatant of viral producers in the presence of 8 μg/ml Polybrene™ (Sigma, St. Louis, Mo.) as described above. Electroporated or infected MEL cells were subsequently split in medium containing 500 μg/ml (active) G418. Single or pool of resistant colonies were isolated and expanded. MEL cells were induced at 37° C. with 5% $CO_2$/95% air in DMEM supplemented with 15% fetal calf serum, 4.5 mg/ml glucose, 2 mM glutamine, 100 IU/ml penicillin, 100 μg/ml streptomycin and 2% dimethylsulfoxide (DMSO) (Sigma, St. Louis, Mo.) for 5 days. Total RNA was extracted by the RNAzol B method according to protocol provided by the manufacturer (Biotecx Laboratories, Inc., Houston, Tex.). Quantitative RNA protection assays were performed with uniformly labeled RNA probes in vitro transcribed with SP6 polymerase (Promega, Madison, Wis.) in the presence of [$\alpha$-$^{32}$P] UTP (Amersham, Arlington Heights, Ill.). A human specific probe was provided by Tom Maniatis (Harvard University, Cambridge, Mass.): the specific protected fragment is 350 bp long and corresponds to the first and second exons of the β-globin mRNA up to the exonic BamH1 site. A murine specific probe was constructed, so that a 145 bp fragment corresponding to the first exon of $\beta_{maj}$-globin mRNA is protected. The first exons of murine $\beta_{maj}$- and $\beta_{min}$-globin genes have extended homology downstream of the "ATG", but diverge extensively in their leader. Because of this pattern of homology and the conditions of our RNA protection assays, the murine specific probe also protects a 115 bp fragment of the murine $\beta_{min}$-globin mRNA. RNA protection assay was performed as described by Sambrook et al., *Molecular cloning; a laboratory manual—2nd ed.*, Cold Spring Harbor Laboratory Press, Cold Spring Harbor, N.Y. (1989) and with the following conditions: 10 μg of total RNA, greater than 5×10$^5$ cpm of each probe in separate reactions, hybridization at 52° C. for 16 hours in [40 mM PIPES, pH 6.4, 400 mM NaCl, 1 mM EDTA, 80% formamide], digestion with 20 μg/ml RNase A (Sigma, St. Louis, Mo.) and 2 μg/ml RNase T1 (Sigma) for 30 minutes at room temperature. Under these conditions, sparse mismatches, such as those present in the mutated human β-globin gene or between homologous regions of murine $\beta_{maj}$- and $\beta_{min}$-globin mRNA, are not detected. Radioactive bands corresponding to the specific protected fragments were scanned using a Phosphor Imager (Molecular Dynamics, Evry Cedex, France), and/or autoradiograms were analyzed with a 2202 Ultrascan laser densitometer (LKB Instruments, Inc., Gaithersburg, Md.). Human β-globin/murine β-globin mRNA ratios were corrected for the number of uridine residues in each probe (factor 2.5) and on a per gene basis. Although the original isolate of aneuploid semi-adherent (APRT-) MEL cells are believed to be pseudo-tetraploid (Chao et al., *Cell*, 32:483–493 (1983)), Southern blot analysis suggests that the MEL cells used in this study are rather pseudo-diploid for the endogenous mouse β-globin genes. Correction (factor 2) was therefore applied to account for this ratio: average of two $\beta_{maj}$- and two $\beta_{min}$-globin genes and only one provirus per cell. Global calculations were made as follows:

$$\frac{\text{Human } \beta}{\text{Murine } \beta_{maj} + min} = \frac{[\text{human } \beta - \text{globin band}] \times 2 \times 100}{[\text{murine } \beta_{maj} + min\text{-globin bands}] \times 2.5}$$

$$\frac{\text{Human } \beta}{\text{Murine } \beta_{maj}} = \frac{[\text{human } \beta - \text{globin band}] \times 2 \times 100}{[\text{murine } \beta_{maj}\text{-globin bands}] \times 2.5}$$

RNA protection assays and Southern blot analysis were performed with a pool of electroporated, G418 selected, and DMSO-induced MEL cells. Results from this experiment suggested that [2×HS2], (HS2+HS3) and (HS2+[2×HS3]) derivatives do not increase β-globin gene expression over HS2 alone; in contrast, addition of HS4 derivatives to HS2 and HS3 appeared to enhance significantly β-globin gene expression. Accordingly, the infection study was limited to the following β-LCR combinations: HS2, [HS2+(4×23 bp of HS2)], [HS2+(4×23 bp of HS2)+HS3], [HS2+HS3+HS4], and [HS2+HS3+(4×CP2 of HS4)]. These various β-LCR derivatives were inserted in the mutated vector optimized for stable proviral transmission. A control vector containing the SV40 enhancer without β-LCR was also included. MEL cells were infected with supernatant from producers in experimental conditions providing up to one integrated provirus per cell, and were subsequently selected with G418. Pools of infected and selected MEL cells of at least 10$^2$ clones were DMSO-induced for five days and subsequently analyzed for human and murine β-globin mRNA expression by RNA protection assay. Transduced human β-globin/murine β-globin mRNA ratios were calculated on a per gene basis, following appropriate corrections. Corrections were applied for specific activity of the probes, and on the basis that the aneuploid MEL cells appear pseudo-diploid for the endogenous murine β-globin genes while containing only one copy of integrated provirus per cell following infection and G418 selection. Cell-type specificity of expression was verified by infection of NIH 3T3 cells: no expression of the transduced β-globin gene was detected. Also, expression of the transduced human β-globin gene was low in non-induced MEL cells. Results obtained with the various constructs are presented in Table I.

Another implication for gene therapy protocols of the mono-or oligo-clonality of bone marrow reconstitutions is the necessity to engraft recipients with only transduced THSC, so that complete and sustained reconstitution with infected cells in 100% of transplanted individuals is achieved. Because a significant proportion of THSC are not infected even by high titer retroviral vectors, as reported by Lemischka et al., *Cell* 45:917–927 (1986); Dzierzak et al., *Nature* 331:35–41 (1988); Karlsson et al., *Proc. Natl. Acad. Sci. USA* 85:6062–6066 (1988); Bender et al., *Mol. Cell. Biol.* 9:1426–1434 (1989); and Fraser et al., *Proc. Natl. Acad. Sci. USA* 89:1968–1972 (1991), it may be therefore desirable to add a step of selection of infected bone marrow cells prior to transplantation. Unfortunately, enhancers/promoters driving NeoR (e.g. LTR, SV40) are believed to be repressed in THSC, as is observed with other stem cells such as embryonic stem (ES) cells, as reported by Hawley et al., *Plasmid*, 22:120–131 (1989). Accordingly, internal enhancers/promoters which are not repressed in ES cells were inserted in the [β-globin/LCR]$^{mut}$ vectors to drive NeoR. These enhancers/promoters include F441 polyoma (F441 Py) enhancer/thymidine kinase (TK) promoter and murine phosphoglycerate kinase-1 (PGK) promoter. In addition, the Tobacco Mosaic Virus (TMV) leader, which is a powerful enhancer of translation (Gallie et al., *Nucleic Acids Res.*, 15:3257–3273 (1987)), was added in some constructs.

Titers of these different vectors upon G418 selection of infected 3T3 cells were compared. NIH 3T3 cells, provided by Jane-Jane Chen (Harvard-MIT HST, MIT, Cambridge, Mass.), were grown at 37° C. with 5% $CO_2$/95% air in DMEM supplemented with 10% calf serum, 100 IU/ml penicillin and 100 μg/ml streptomycin. NIH 3T3 cells were infected with various dilutions of filtrated viral supernatant in the presence of 8 μg/ml Polybrene™ (Sigma, St. Louis, Mo.) as described by Danos and Mulligan, *Proc. Natl. Acad. Sci. USA* 85:6460–6464 (1988). Cells were subsequently split in medium containing 500 μg/ml (active) G418. Resistant colonies were counted, and titers estimated by standard calculations previously described (Danos and Mulligan, supra 1988). Proviral transmission was tested by Southern analysis (Sambrook et al., *Molecular cloning: a laboratory manual*—2nd ed. Cold Spring Harbor Laboratory Press, Cold Spring Harbor, N.Y., 1989), with neoR and β-globin specific probes and appropriate controls.

Titers were found similar for SV40, F441 Py/TK, and F441 Py/TK/TMV. In contrast, PGK increased viral titer by over five times as compared to the first group (Table I). Because these heterologous enhancers are positioned in [β-globin/LCR]$^{mut}$ vectors next to LCR derivatives, possible influence exerted by these heterologous enhancers on β-LCR derivatives for transcription of the transduced β-globin gene was also investigated. Results of this experiment indicate that heterologous enhancers are not neutral for β-globin expression when linked to HS2. The global level of enhancement provided by the combination [HS2+ heterologous enhancer] increases in the following order: SV40, PGK, and F441 Py/TK (Table I).

β-globin Expression is Partially Independent of the Sites of Chromosomal Integration Since mono- or oligo-clonality is frequently observed in long-term reconstituted hematopoietic systems (Lemischka et al., *Cell* 45:917–927 (1986); Fraser et al., *Proc. Natl. Acad. Sci. USA* 89:1968–1972 (1991)), it is essential to obtain expression of the transduced β-globin gene relatively independently of the site of chromosomal integration, so that consistent and sustained β-globin gene expression is achieved. Grosveld et al., *Cell*, 51:975–985 (1987); Collis et al., *EMBO J.* 9:233–240 (1990); Philipsen et al., *EMBO J.* 9:2159–2167 (1990); Talbot et al., *EMBO J.* 9:2169–2178 (1990); and Pruzina et al., *Nucleic Acids Res.* 19:1413–1419 (1991) have reported that each of the HS sites, individually or in association, are able to confer position-independence in MEL cells and transgenic mice, although incomplete position-independence has been also reported by Curtin et al., *Proc. Natl. Acad. Sci. USA*, 86:7082–7086 (1989); Forrester et al., *Proc. Natl. Acad. Sci. USA*, 86:5439–5443 (1989); Ryan et al., *Genes Dev.*, 3:314–323 (1989); and Novak et al., *Proc. Natl. Acad. Sci. USA*, 87:3386–3390 (1990). Accordingly, the variability of β-globin mRNA expression in six independent MEL cell clones, following infection and G418 selection, was tested. [β-globin/HS2/PGK]$^{mut}$ was the focus of the study, based on the assumption that position independence would be reinforced by additional HS fragments if it was observed with one isolated HS site.

Complete position-independence was not observed, but the variation appears relatively moderate, as shown by Table II.

TABLE II

Variability of expression of the transduced human β-globin gene in independent MEL cell clones infected with [β-globin/HS2/PGK]$_{mut}$.

| Clone numbers | Human β / Murine β$_{maj}$ + $_{min}$ | Human β / Murine β$_{maj}$ | Murine β$_{maj}$ / Murine β$_{min}$ |
|---|---|---|---|
| 1 | 32% | 70% | 0.83 |
| 2 | 48% | 108% | 0.81 |
| 3 | 34% | 89% | 0.60 |
| 4 | 40% | 89% | 0.82 |
| 5 | 26% | 59% | 0.82 |
| 6 | 21% | 54% | 0.65 |

Independent clones following infection and G418 selection. Corrected values for specific activities of the probes and on a per gene basis (one proviral copy per cell in pseudo-diploid MEL cells).

Treatment of β-globin Disorders by Gene Transfer

The retroviral vector described herein is useful for the treatment of β-globin disorders such as β-thalassemias and sickle cell anemia by gene transfer.

Gene transfer is achieved by infecting autologous totipotent hematopoietic stem cells (THSC) with the retroviral vector in accordance with methods known to those skilled in the art.

Modifications and variations of the present invention, retroviral vectors for transducing human β-globin gene and β-locus control region derivatives, will be obvious to those skilled in the art from the foregoing detailed description. Such modifications and variations are intended to come within the scope of the appended claims.

---

We claim:

1. A method of making a retroviral vector for transducing β-globin genes and β-LCR sequences comprising the steps of:

(a) providing a retroviral vector in combination with a β-globin gene and an effective portion of the HS2 enhancer of the β-LCR, with or without additional β-LCR sites, to achieve transduction and expression of the β-globin gene, and (b) modifying a DNA sequence of the second intron of the β-globin gene, and complementary/reverse splice-signals, polyadenylation signals, or combinations thereof, to remove or inactivate splicing sites or polyadenylation signals of the transduced β-globin gene or β-LCR, to form a retroviral vector characterized by:

i) stability of proviral transmission upon infection of cell-lines and murine bone marrow cells, ii) viral titer effective to achieve infection of bone marrow cells, and iii) high erythroid expression of the transduced human β-globin gene.

2. The method of claim 1 wherein the effective viral titer is greater than $10^5$ resistant colonies per ml of viral supernatant under standard conditions.

3. The method of claim 1 wherein the high erythroid expression is greater than 50% of a human β-globin to murine $β_{maj}$-globin mRNA ratio as assessed in dimethyl sulfoxide-induced MEL cells.

4. The method of claim 1 wherein said retroviral vector comprises:

(a) a left and right long terminal repeat (LTR), (b) a tRNA primer binding site for initiation of synthesis of viral minus strand strong-stop;

(c) a polypurine track primer binding site for initiation of synthesis of viral plus strand strong-stop, and (d) a packaging signal.

5. The method of claim 4 wherein said packaging signal extends into a gag region.

6. The method of claim 4 wherein said right LTR comprises a deletion in a U3 region yielding a self-inactivating vector upon reverse transcription.

7. The method of claim 1 wherein said retroviral vector is a splicing vector, comprising functional splicing signals leading to genomic and sub-genomic transcripts.

8. The method of claim 1 wherein said retroviral vector is not a splicing vector.

9. The method of claim 1 wherein said retroviral vector has a selectable marker.

10. The method of claim 9 wherein said selectable marker is driven by an internal enhancer/promoter.

11. The method of claim 10 wherein said selectable marker is driven by the left LTR.

12. The method of claim 9 wherein said selectable marker is placed in a splicing retroviral vector.

13. The method of claim 9 wherein said selectable marker is selected from the group consisting of a neomycin/G418 resistance gene, a hygromycin resistance gene, a puromycin resistance gene, a phleomycin resistance gene, a dihydrofolate reductase gene, a multidrug-resistance gene, and a gene for an enzyme.

14. The method of claim 9 wherein said selectable marker is a molecule that interacts with a substrate to produce a colored cell.

15. The method of claim 14 wherein said selectable marker is the gene encoding β-galactosidase.

16. The method of claim 9 wherein said selectable marker is a molecule expressed at the cell membrane.

17. The method of claim 1 wherein said modifications are selected from the group consisting of deletions, additions, and substitutions of nucleotides in the DNA sequence of the second intron of the β-globin gene, complementary splice-signals or polyadenylation signals of the transduced β-globin gene or LCR.

18. The method of claim 1 wherein said β-globin gene is modified within the second intron of the β-globin gene, while maintaining correct splicing of this intron as well as normal expression of the β-globin transgene as compared to the non-deleted Intron 2 containing β-globin gene.

19. The method of claim 1 wherein said transduced β-globin gene or β-LCR contain partial deletions, substitutions, mutations or modifications of at least one of the complementary/reverse 5' splice-sites or 3' splice-sites or branchpoint signals or polyadenylation signals.

20. The method of claim 1 wherein a transcriptionally active HS2 fragment is incorporated, in a single or duplicated form or in association with other β-LCR or heterologous enhancer sequences, in any position or orientation.

21. The method of claim 1 wherein a transcriptionally active HS3 fragment is incorporated, in a single or duplicated form or in association with other β-LCR derivatives or heterologous enhancer sequences, in any position or orientation.

22. The method of claim 1 wherein a transcriptionally active HS4 fragment is incorporated, in a single or duplicated form or in association with other β-LCR or heterologous enhancer sequences, in any position or orientation.

23. A retroviral vector for transducing β-globin genes and β-LCR sequences comprising:

(a) a left and a right long terminal repeat (LTR), (b) a tRNA primer binding site for initiation of synthesis of vital minus strand strong-stop, (c) a polypurine track primer binding site for initiation of synthesis of viral plus strand strong-stop, (d) a packaging signal, (e) a β-globin gene, and (f) an effective portion of the HS2 enhancer of the β-LCR to achieve transduction and expression of the β-globin gene, wherein the DNA sequence of the second intron of the β-globin gene is modified, and complementary/reverse splice-signals or polyadenylation signals of the transduced β-globin gene or β-LCR are modified, or both are modified, to inactivate or remove splicing sites or polyadenylation signals within the vector so that the retroviral vector exhibits stability of proviral transmission upon infection of cell-lines and murine bone marrow cells, viral titer effective to achieve infection of bone marrow cells, and high erythroid expression of the transduced human β-globin gene.

24. The retroviral vector of claim 23 wherein the effective viral titer is greater than $10^5$ resistant colonies per ml of viral supernatant under standard conditions and the high erythroid expression is greater than 50% of a human β-globin to murine $β_{maj}$-globin mRNA ratio as assessed in dimethyl sulfoxide-induced MEL cells.

25. The retroviral vector of claim 23 wherein said packaging signal extends into a gag region.

26. The retroviral vector of claim 23 wherein said retroviral vector is a splicing vector comprising functional splicing signals leading to genomic and sub-genomic transcripts.

27. The retroviral vector of claim 23 wherein said retroviral vector further comprises a selectable marker.

28. The retroviral vector of claim 23 wherein said modifications are selected from the group consisting of deletions, additions, and substitutions of nucleotides in the DNA sequence of the second intron of the β-globin gene, complementary splice-signals or polyadenylation signals of the transduced β-globin gene or LCR.

29. The retroviral vector of claim 23 wherein said selectable marker is driven by an internal enhancer/promoter.

30. The retroviral vector of claim 23 wherein said selectable marker is driven by the left LTR.

31. The retroviral vector of claim 23 wherein said selectable marker is placed in a splicing retroviral vector.

32. The retroviral vector of claim 23 wherein said selectable marker is selected from the group consisting of a neomycin/G418 resistance gene, a hygromycin resistance gene, a puromycin resistance gene, a phleomycin resistance gene, a dihydrofolate reductase gene, a multidrug-resistance gene, and a gene for an enzyme.

33. The retroviral vector of claim 23 wherein said selectable marker is a molecule that interacts with a substrate to produce a colored cell.

34. The retroviral vector of claim 33 wherein said selectable marker is the gene encoding β-galactosidase.

35. The retroviral vector of claim 23 wherein said selectable marker is a molecule expressed at the cell membrane.

36. The retroviral vector of claim 23 wherein said right LTR comprises a deletion in a U3 region yielding a self-inactivating vector upon reverse transcription.

37. The retroviral vector of claim 23 wherein said β-globin gene is modified within the second intron of the β-globin gene, while monitoring correct splicing of this intron as well as normal expression of the β-globin transgene as compared to the non-deleted Intron 2 containing β-globin gene.

38. The retroviral vector of claim 23 wherein said transduced β-globin gene or β-LCR sequences contain partial deletions, substitutions, mutations or modifications of at least one of the complementary/reverse 5' splice-sites or 3' splice-sites or branchpoint signals or polyadenylation signals.

* * * * *